United States Patent
Park (10) Patent No.: US 9,414,945 B2
(45) Date of Patent: Aug. 16, 2016

(54) GASTRIC BAND SECURING DEVICE AND GASTRIC BAND COMPRISING SAME

(71) Applicant: Yun Chan Park, Seongnam-si (KR)

(72) Inventor: Yun Chan Park, Seongnam-si (KR)

( * ) Notice: Subject to any disclaimer, the term of this patent is extended or adjusted under 35 U.S.C. 154(b) by 112 days.

(21) Appl. No.: 14/494,034

(22) Filed: Sep. 23, 2014

(65) Prior Publication Data

US 2015/0012020 A1    Jan. 8, 2015

Related U.S. Application Data

(63) Continuation of application No. PCT/KR2013/005093, filed on Jun. 10, 2013.

(30) Foreign Application Priority Data

Jun. 28, 2012    (KR) .................. 10-2012-0070164

(51) Int. Cl.
| | | |
|---|---|---|
| *A61F 2/00* | (2006.01) | |
| *A61F 5/00* | (2006.01) | |
| *A61B 17/122* | (2006.01) | |
| *A61B 17/128* | (2006.01) | |
| *A61F 2/04* | (2013.01) | |

(52) U.S. Cl.
CPC ............... *A61F 5/005* (2013.01); *A61B 17/122* (2013.01); *A61B 17/128* (2013.01); *A61F 2/04* (2013.01); *A61F 5/0053* (2013.01); *A61F 5/0079* (2013.01)

(58) Field of Classification Search
CPC ............ A61F 2/00–2/30; A61F 5/00–5/0086; A61F 5/005–5/0006
USPC ...................... 600/31, 37; 606/151
See application file for complete search history.

(56) References Cited

U.S. PATENT DOCUMENTS

| 6,694,982 B2 | 2/2004 | Latour | |
|---|---|---|---|
| 2002/0169494 A1* | 11/2002 | Mertens | A61F 2/958 623/1.11 |
| 2004/0158272 A1 | 8/2004 | Hofle et al. | |
| 2006/0074439 A1* | 4/2006 | Garner | A61F 5/003 606/153 |
| 2006/0129027 A1* | 6/2006 | Catona | A61F 5/0056 600/37 |
| 2007/0249894 A1* | 10/2007 | Nicholson | A61B 17/04 600/37 |
| 2010/0145324 A1* | 6/2010 | Nihalani | A61F 5/0013 606/14 |
| 2012/0108892 A1* | 5/2012 | Beckman | A61F 5/003 600/37 |

FOREIGN PATENT DOCUMENTS

| JP | 2008-296013 A | 12/2008 |
|---|---|---|
| KR | 10-2007-0009493 A | 1/2007 |

OTHER PUBLICATIONS

"Technical Data Sheet Permatex Black Silicone Adhesive Sealant" Permatex, Feb. 2009. Web. Feb. 25, 2016.*
International Search Report for PCT/KR2013/005093 dated Sep. 26, 2013 [PCT/ISA/210].

* cited by examiner

*Primary Examiner* — John Lacyk
(74) *Attorney, Agent, or Firm* — Sughrue Mion, PLLC (57) ABSTRACT

Provided are a gastric band securing device and a gastric band including the gastric band securing device which includes: a main body configured to be attached to a portion of a stomach; and a linking part having one end configured to be connected to the main body, and the other end configured to be connected to the gastric band configured to wrap around an inlet of the stomach.

20 Claims, 8 Drawing Sheets

GASTRIC BAND SECURING DEVICE AND GASTRIC BAND COMPRISING SAME

CROSS-REFERENCE TO RELATED PATENT APPLICATION

The present application is a Continuation of PCT International Application No. PCT/KR2013/005093, filed on Jun. 10, 2013, and claims priority from Korean Patent Application No. 10-2012-0070164, filed on Jun. 28, 2012, the disclosures of which are incorporated herein by reference in their entirety.

BACKGROUND

1. Field Apparatuses consistent with exemplary embodiments of the inventive concept relate to a gastric band securing device and a gastric band comprising the same.

2. Description of Related Art

A gastric band is a surgical device which wraps a lower portion of an esophagus, that is, an upper portion of a stomach. The gastric band minimizes a volume of the stomach and slows down inflow speed of foods.

One of complications accompanying a gastric band surgery is a band slip. The band slip means that gastric tissues under the gastric band are crawled up and a lot of gastric tissues are jammed in the gastric band, thereby preventing a person with the gastric band from eating foods.

A widely used method for preventing the band slip is a gastro-gastric suture by which gastric tissues above and under the gastric band are sutured and fixed with each other. For example, if a portion of the gastric tissues under the gastric band is pulled above the gastric band and is sutured with the gastric tissues above the gastric band, the gastric band may not move and the gastric tissues above and under the gastric band are prevented from moving freely in the gastric band because the sutured gastric tissues wrap a part of the gastric band.

While the gastro-gastric may be able to minimize the band slip, tension may occur when the gastric tissues above and under the gastric band are sutured with each other. In addition, tension occurs at a sutured portion as the gastric tissues are pulled down after the suture. Therefore, the sutured portion may be damaged. Further, the gastric band may damage stomach walls along a position through which a fine needle and thread passes in the suture. This is referred to as an erosion (or intra-gastric migration) that is one of serious complications that may occur after the gastric band surgery.

In addition, the gastric tissues above and under the gastric band are sutured with each other when performing an operation using the related art gastric band. Since the sutured portion approaches a part of the gastric band tightening the stomach very closely, however, possibility of the erosion may further increase. In some cases, dehiscence occurs and gut contents may be spilt out, which causes peritonitis.

SUMMARY

One or more exemplary embodiments of the inventive concept provide a solution for fixing a gastric band at a stomach stably, keeping a portion of the stomach tightened by the gastric band form being wounded, and preventing a band slip and an erosion.

According to an aspect of an exemplary embodiment, there is provided a gastric band securing device which may include: a main body configured to be attached to a portion of a stomach; and a linking part having one end configured to be connected to the main body, and the other end configured to be connected to a gastric band configured to wrap around an inlet of the stomach.

Hardness of the linking part may be lower than that of the main body.

The main body and the linking part may be made from silicone.

The portion of the stomach to which the main body is connected is disposed below the gastric band wrapping around the inlet of the stomach.

At least one hole may be formed at the main body and the hole is configured such that an upper part of the portion of the stomach is exposed through the hole and sutured with a lower part of the portion of the stomach disposed below the main body.

The at least one home may include a plurality of holes.

The linking part may have an annular shape and configured to wrap the gastric band to be connected to the gastric band.

The portion of the stomach to which the main body is connected is disposed below the gastric band wrapping around the inlet of the stomach.

The main body may have a circular cross-section.

According to an aspect of another exemplary embodiment, there is provided a gastric band which may include: a band body and the above gastric band securing device.

The gastric band may further include a tube mounted on an inside of the band body, wherein the tube is configured to receive and output a fluid used to control a diameter of the inlet of the stomach.

A gap between a lower end portion of the tube and a lower end portion of the gastric band securing device may be about 0.2-4 cm.

According to the exemplary embodiments, the gastric band may be fixed stably by the gastric band securing device for a long time.

In addition, since the gastric band tightening gastric tissues and the main body sutured with the gastric tissues are far away, possibility of an erosion can be minimized.

In addition, since the linking part is made from silicone having elasticity, expansion of the tube may not be hindered when the tube of the gastric band expands. Therefore, the gastric band can tighten the entire gastric tissues contacting with the gastric band with uniform force.

In addition, since the main body is fixed to the gastric tissues under the gastric band, the gastric tissues may not be affected by pressure even though the pressure is applied to the gastric tissues above the gastric band by food intake after an operation. Therefore, there is no possibility of dehiscence due to food intake after the operation.

In addition, since a main body is fixed by suturing the gastric tissues exposed through the hole of the main body with the gastric tissues under the main body, the gastric tissues and the main body are joined stably. In addition, since the gastric band is detached easily by cutting the main body if removal of the gastric band is required, the gastric band can be easily removed.

BRIEF DESCRIPTION OF THE DRAWINGS

The above and other aspects will become more apparent by describing in detail exemplary embodiments thereof with reference to the attached drawings, in which.

DETAILED DESCRIPTION OF THE EXEMPLARY EMBODIMENTS

The inventive concept will be described more fully hereinafter with reference to the accompanying drawings, in which exemplary embodiments thereof are shown. As those skilled in the art would realize, the described embodiments may be modified in various different ways, all without departing from the spirit or scope of the inventive concept. Like reference numerals designate like elements throughout the specification.

A gastric band securing device and a gastric band including the same according to an exemplary embodiment will be described in detail with reference to FIG. 1 to FIG. 3.

Figure 1:
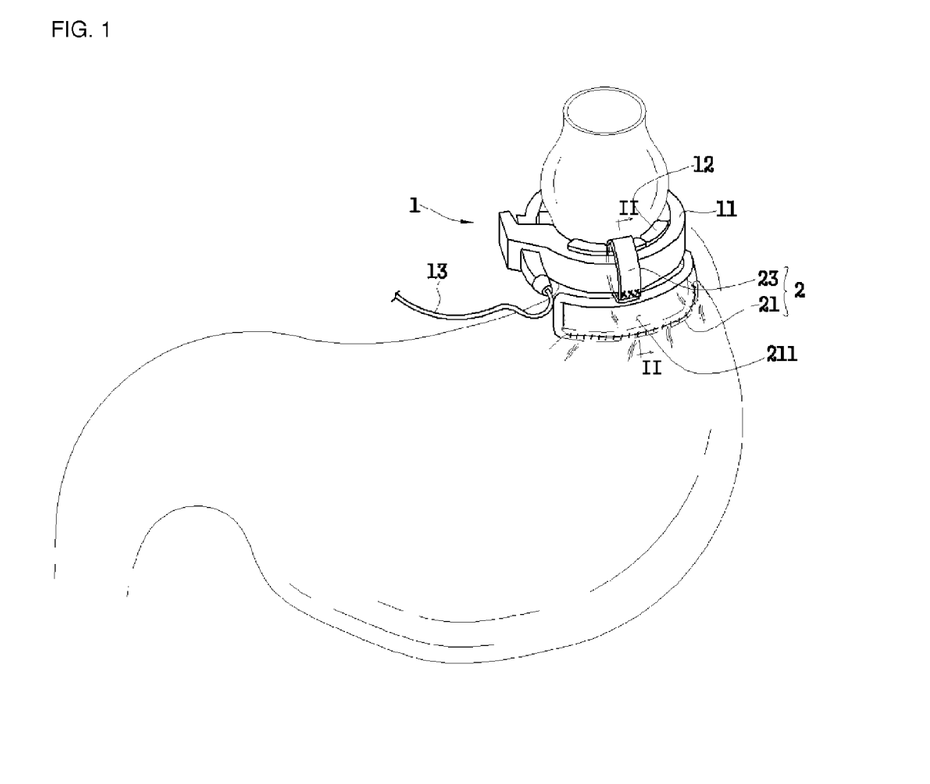
FIG. 1 is a schematic diagram of a gastric band in use, according to an exemplary embodiment.
Figure 2:
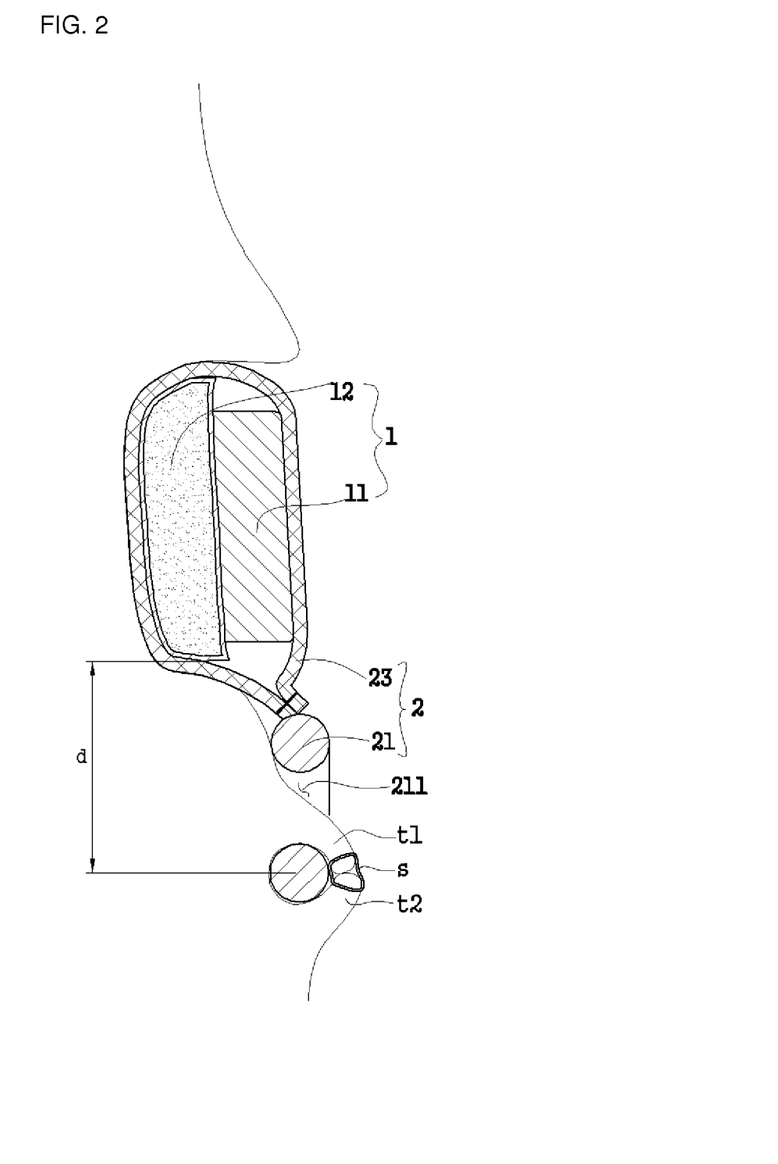
FIG. 2 is a cross-sectional view taken along a ling II-II in FIG. 1, according to an exemplary embodiment.
Figure 3:
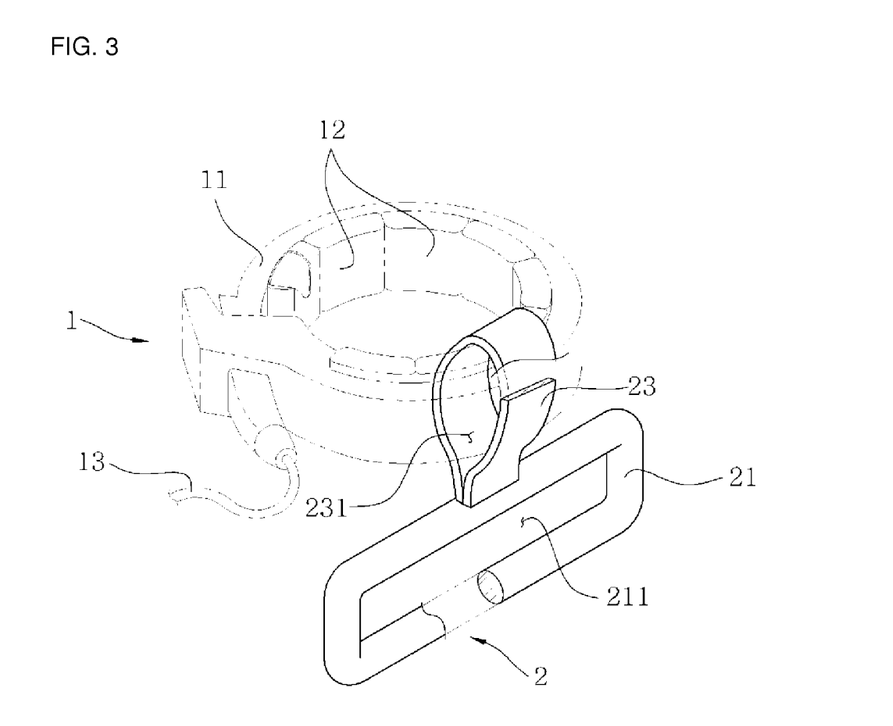
FIG. 3 is a perspective view of a gastric band securing device shown in FIG. 1, according to an exemplary embodiment.

FIG. 1 illustrates a gastric band fixed to a stomach, FIG. 2 is a cross-sectional view taken along a ling II-II in FIG. 1, and FIG. 3 is a perspective view of a gastric band securing device shown in FIG. 1.

Referring to FIG. 1 to FIG. 3, the gastric band securing device 2 according to the present exemplary embodiment is adapted to fix the gastric band 1 wrapping a part of the stomach. The gastric band securing device 2 includes a main body 21 and a linking part 23.

The gastric band 1 wraps a portion just below an esophagus, that is, an upper portion of the stomach so as to adjust an interior diameter of the stomach. The gastric band 1 includes a body 11 and a tube 12, according to an exemplary embodiment. The body 11 has a band shape having both end portion divided from each other. A jointing groove is formed at one end of the body 11 and a jointing protrusion is formed at the other end of the body 11. If the jointing protrusion is jointed with the jointing groove, the body 11 is formed to be an annular shape.

The tube 12 is coupled to an inner surface of the body 11. Unit members of the tube 12 are sequentially disposed along a length direction of the body 11. Inner spaces of the unit members are connected with each other. A supply line 13 for supplying fluid into the tube 12 is connected thereto. The fluid can be supplied to or exhausted from the tube 12 through the supply line 13. An expansion amount of the tube 12 can be controlled according to a supply amount of the fluid, and thus, the interior diameter of the stomach contacting with the tube 12 can be also controlled. The gastric band 1 may not have the tube 12, according to another exemplary embodiment.

The main body 21 and the linking part 23 can be made from medical silicone. The medical silicone may be pasteurized by heat, may not be thermally degraded in a human body, and may not adhere to biological tissues. The main body 21 and the linking part 23 made from the silicone can be deformed freely.

Strength or hardness of the main body 21 and the linking part 23 made from the medical silicone may be the same or different. If the hardness of the main body 21 is different from that of the linking part 23, it is preferable, but not necessary, that the hardness of the linking part 23 is lower than that of the main body 21. For example, the hardness of the main body 21 may be about 35 A to 45 A and the hardness of the linking part 23 may be about 15 A to 20 A. Herein, the hardness is represented by 'A' that is a durometer unit, wherein the softest one is represented as 0 and the hardest one is represented as 100.

If the hardness of the main body 21 is lower than 35 A, it is very difficult to fix gastric tissues to one position. In addition, if the hardness of the linking part 23 is higher than 20 A, the tube 12 is hindered from being expanded. That is, a gastric band surgery is effective if the fluid is supplied into the tube 12 so as to tighten the gastric tissues suitably after the gastric band surgery. If the hardness of the linking part 23 is higher than 20 A, however, the tube 12 facing the gastric tissues across the linking part 23 cannot sufficiently tighten the stomach. Therefore, it is preferable, but not necessary, that the hardness of the linking part 23 is lower than 20 A so that the linking part 23 is comparably soft.

The main body 21 has a predetermined size and area, and a hole 211 is formed at a center portion of the main body 21. The main body 21 has a circular cross-section. Referring to FIG. 3, the main body 21 has a solid rod shape but may have a hollow rod shape. Since the main body 21 has a curved configuration, the main body 21 can contact with a surface of the stomach smoothly. Thereby, a damage of the tissues due to friction may be minimized.

Figure 4:
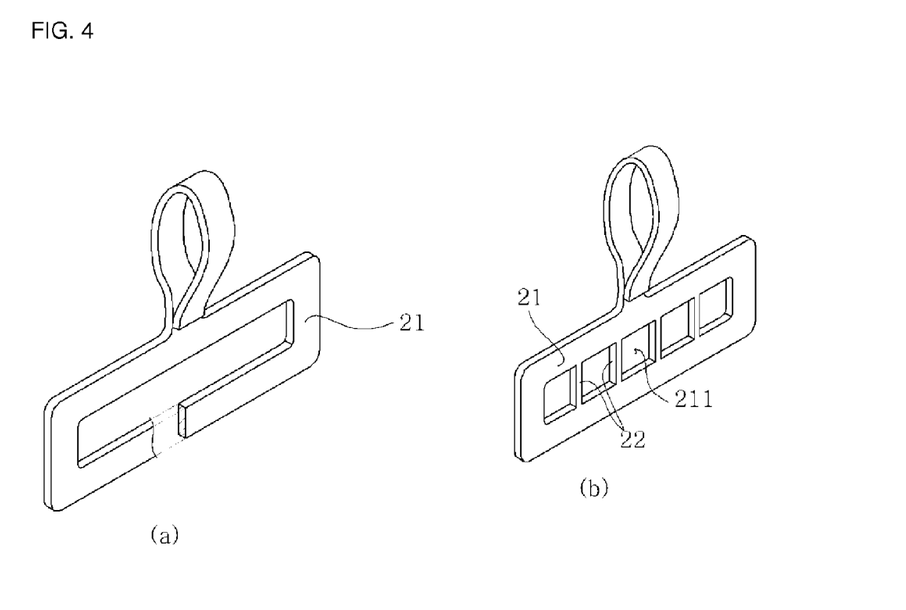
FIG. 4 to FIG. 8 are perspective views of a gastric band securing device according to exemplary embodiments.

However, the cross-section of the main body 21 may be, as shown in FIGS. 4A, a flat quadrangle. Additionally, the shape and the configuration of the main body 21 may be changed in various ways.

Figure 5:
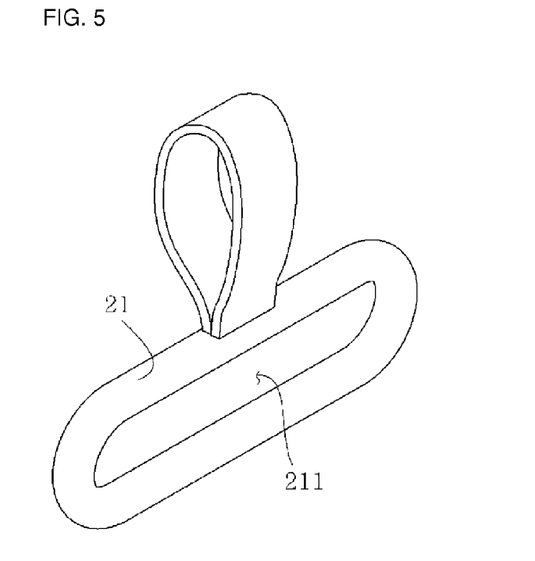

A front view of the main body 21 is a rectangle. However, as shown in FIG. 5, a front view of each side portion of the main body 21 may be a half circle.

The main body 21 is disposed apart from the gastric band 1 by a predetermined distance d and contacts with an exterior surface of the stomach. A region of the gastric band 1 tightening the tube 12 (hereinafter, it will be called a 'tightening region') is spaced from a region where the main body 21 and the gastric tissues are sutured (hereinafter, it will be called a 'sutured region') by about 0.2-4 cm. If the distance between the tightening region and the sutured region is smaller than about 0.2 cm, a tension occurs at the sutured region and there is a high possibility of an erosion. If the distance between the tightening region and the sutured region is larger than 4 cm, the gastric band 1 may not be fixed stably.

If the main body 21 contacts the gastric tissues, the gastric tissues are exposed through the hole 211 of the main body 21. In order to fix the main body 21 to the stomach, the gastric tissues t1 exposed through the hole 211 and the gastric tissues t2 under the main body 21 are sutured by suture materials so as to wrap a lower portion of the main body 21 (refer to FIG. 2). In this way, the gastric tissues wrap on a curved surface of the main body 21 smoothly, stress does not occur at the gastric tissues and the main body 21 can be fixed stably for a long time. In addition, if it is necessary to remove the gastric band 1, the main body 21 can be easily detached from the gastric tissues by cutting the main body 21.

If the main body 21 and the gastric tissues are directly sutured, the gastric tissues of a human body and the main body 21 of a foreign material may not be sutured as one organ. Therefore, the main body 21 and the gastric tissues are fixed only by strength of the suture materials. In this case, since each suture material must be separated when removing the gastric band, a time for removing the gastric band is long and the operation has a high level of difficulty.

Figure 6:
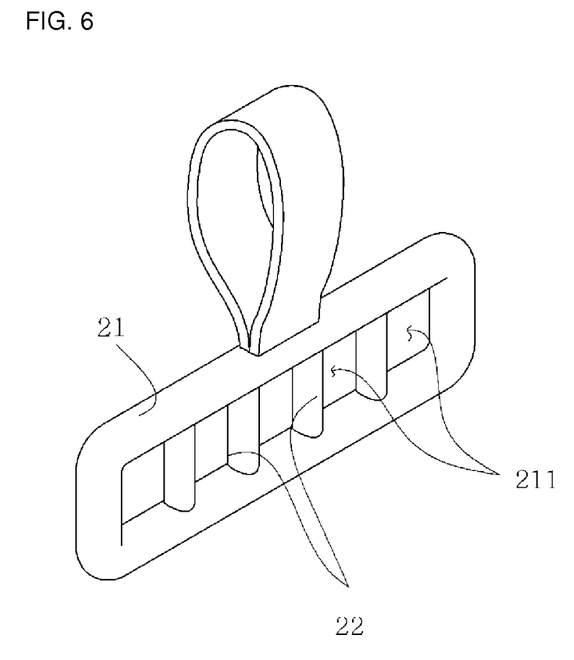

As shown in FIG. 4B and FIG. 6, a plurality of reinforcing parts 22 may be arranged apart from each other along a length direction of the main body 21 in the hole 211 of the main body 21. However, the plurality of reinforcing parts 22 may be arranged in the main body 21 vertically. The hole 211 is divided into a plurality sections by the reinforcing parts 22. The plurality of reinforcing parts 22 minimizes movements of the gastric tissues around the hole 211 of the main body 21 and a force applied to the sutured region. Therefore, a damage of the sutured region due to the movements of the gastric tissues may be reduced.

Figure 7:
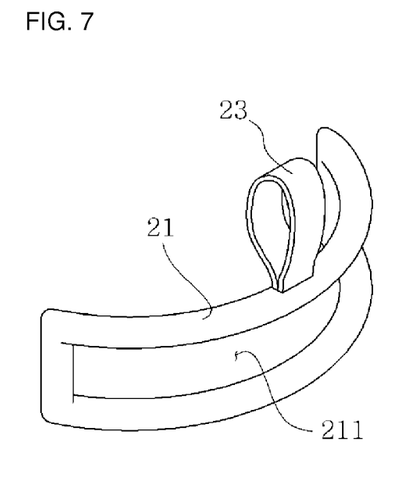

In addition, as shown in FIG. 7, the main body 21 may be originally formed to have a curved shape by flexible bending for the main body 21 to correspond an exterior surface of the stomach. If the main body 21 has the curved shape, a contacting force with the exterior surface of the stomach may be improved. In addition, since an elastic force for returning the main body to an initial position in a fixed state to the stomach, the main body may be stably fixed to the stomach.

Referring to FIG. 1 to FIG. 3 again, the linking part 23 connects the main body 21 with the gastric band 1. The linking part 23 is connected to the main body 21. The linking part 23 may be integrally formed with the main body 21. However, the linking part 23 and the main body 21 may be formed as separate members and may be connected with each other. At this time, the linking part 23 and the main body 21 may be connected by a glue or a suture.

The linking part 23 has an annular shape. The annular shape may be elliptical or circular. A portion of the gastric band 1 is disposed in a ring hole 231 of the linking part 23.

Figure 8:
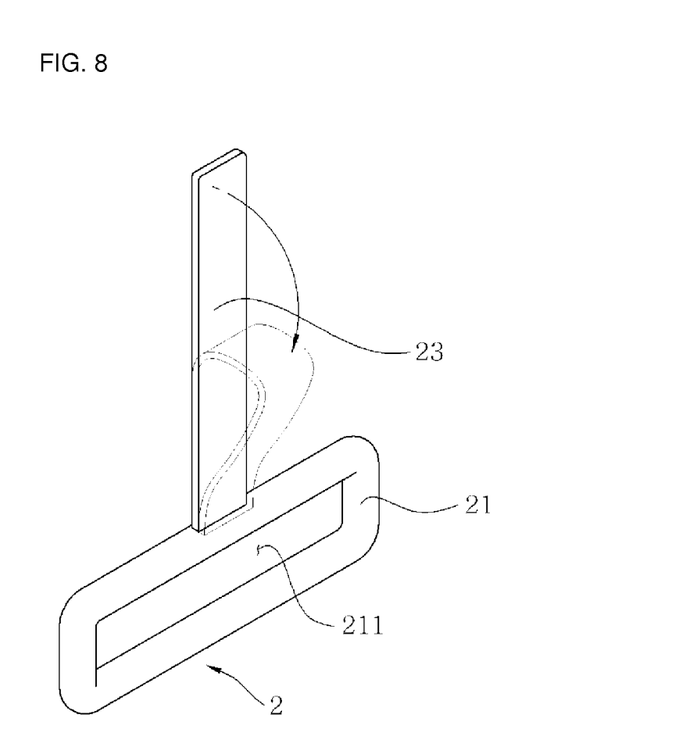

Referring to FIG. 8, the linking part 23 may have a band shape. That is, one end of the linking part 23 is fixed to the main body 21 and the other end of the linking part 23 is a free end. The free end of the linking part 23 wraps the portion of the gastric band 1, and then, is fixed to the linking part 23 or the main body 21.

The linking part 23 can be deformed according to the shape of the tube 12 which can expand or contract. Since the hardness of the linking part 23 is lower than that of the main body 21, the linking part 23 does not hinder expansion or contraction of the tube 12. A cross-section of the linking part 23 has a flat panel shape. However, the shape of the linking part 23 may be changed in various ways.

An operation method using the gastric band securing device as described above will be described with reference to FIG. 1 to FIG. 3.

Before both end portions of the gastric band 1 wrapping the upper portion of the stomach are connected with each other, the gastric band 1 penetrates the ring hole 23 of the linking part 23. At this time, the main body 21 is positioned under the body 11. After that, the both end portions of the gastric band 1 are coupled with each other. As shown in FIG. 8, however, if the linking part 23 has the band shape, the linking part 23 and the gastric band 1 can be connected after the gastric band 1 is changed into the annular shape.

After that, the main body 21 contacts the exterior surface of the stomach and the gastric tissues t1 exposed through the hole 211 of the main body 21 are sutured with the gastric tissues t2 under the main body 21. Accordingly, the gastric tissues are arranged to wrap the main body 21. If the gastric band 1 is required to be removed, the main body 21 is cut such that the cut main body 21 can be easily detached from the sutured region.

Lastly, the fluid is supplied to the tube 12. Therefore, the tube 12 tightens the gastric tissues so as for the stomach to have a target interior diameter.

Figure 9:
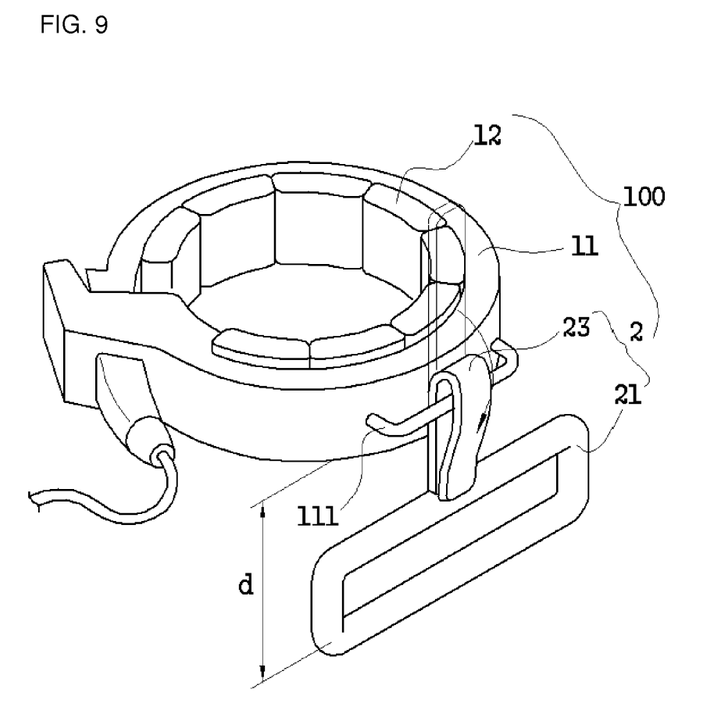
FIG. 9 to FIG. 11 are perspective views of a gastric band according to other exemplary embodiments.

Referring to FIG. 9, a gastric band according to another exemplary embodiment will be described.

Referring to FIG. 9, the gastric band 100 according to the present exemplary embodiment includes the body 11, the tube 12, a coupled portion 111 and the gastric band securing device 2.

The body 11, the tube 12 and the gastric band securing device 2 according to the present exemplary embodiment are substantially the same as those according to the exemplary embodiment illustrated in FIG. 1 to FIG. 3.

However, the present exemplary embodiment further includes the coupled portion 111. The coupled portion 111 is protruded from an exterior surface of the band body 11, and the linking part 23 is coupled with the coupled portion 111.

The linking part 23 of the gastric band securing device 2 according to the present exemplary embodiment has the band shape shown in FIG. 8. Since the linking part 23 according to the present exemplary embodiment is coupled to the exterior of the body 11 and does not contact the tube 12, the linking part 23 having greater hardness or strength than the previous exemplary embodiments may be used.

Figure 10:
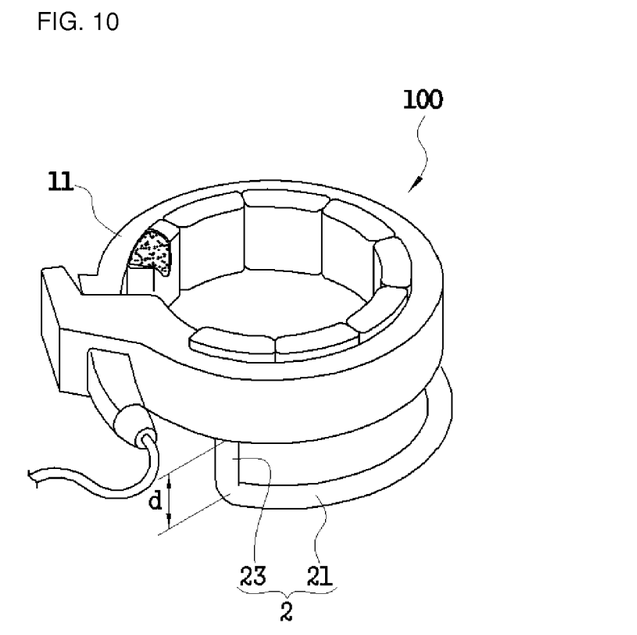
Figure 11:
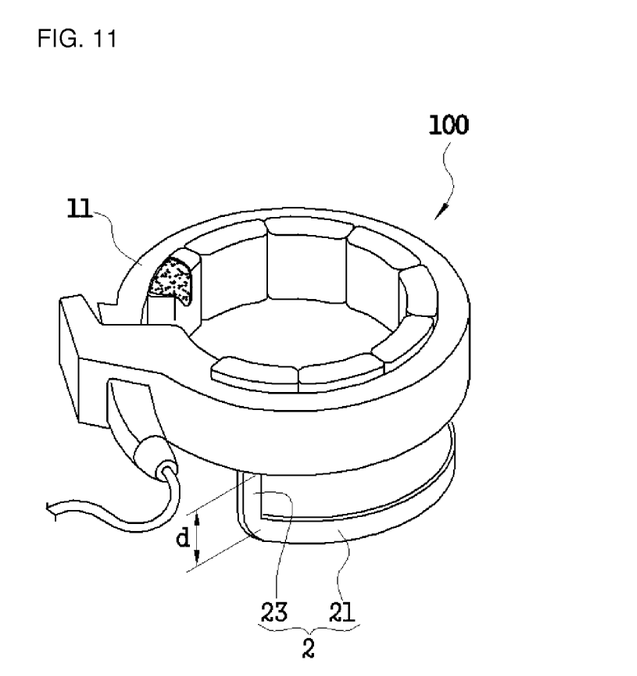

According to other exemplary embodiments as shown in FIGS. 10 and 11, a gastric band securing device 2 may be directly formed at a gastric band 100 to constitute a single, integral unit together with the gastric band 100. Referring to FIGS. 10 and 11, two linking parts 23 (only one linking part 23 is shown in FIGS. 10 and 11) are formed to be protruded from a bottom portion of the gastric band 100. One end of each linking part 23 is attached to the bottom portion of the gastric band 100, and the other ends of the two linking parts 23 are connected to each other by a main body 21 to form a hole (corresponding to the hole 211 in FIGS. 1-3) through which gastric tissues exposed through this hole and gastric tissues disposed under the main body 21 are sutured to wrap the main body 21.

A cross-section of the gastric band securing device 2 may have a circular shape as shown in FIG. 10 or a flat quadrangular shape as shown in FIG. 11.

Since a process for connecting the gastric band securing device 2 with the body 11 is not required if the gastric band securing device 2 is directly formed at the body 11, an operating time may be shortened.

While this inventive concept has been described in connection with what is presently considered to be practical exemplary embodiments, it is to be understood that the inventive concept is not limited to the disclosed embodiments, but, on the contrary, is intended to cover various modifications and equivalent arrangements included within the spirit and scope of the appended claims.

What is claimed is:

1. A gastric band securing device comprising:
   a main body configured to be attached to a portion of a stomach; and
   a linking structure having one end configured to be connected to the main body, and the other end configured to be connected to a gastric band configured to wrap around an inlet of the stomach,
   wherein at least one hole is formed at the main body and the at least one hole has a size allowing a gastric tissue of the stomach exposed through the at least one hole and another gastric tissue of the stomach positioned below the main body, when the main body is attached to the portion of the stomach, to be connected to each other and wrap around a lower portion of the main body.

2. The gastric band securing device of claim 1, wherein hardness of the linking structure is lower than that of the main body.

3. The gastric band securing device of claim 1, wherein the main body and the linking structure are made from silicone.

4. The gastric band securing device of claim 1, wherein the at least one hole is configured to allow the gastric tissue and the other gastric tissue to be sutured to each other.

5. The gastric band securing device of claim 1, wherein the at least one hole is configured such that an upper part of the portion of the stomach is exposed through the at least one hole and sutured with a lower part of the portion of the stomach disposed below the main body.

6. The gastric band securing device of claim 1, wherein the at least one hole comprises a plurality of holes.

7. The gastric band securing device of claim 1, wherein the linking structure has an annular shape and configured to wrap the gastric band to be connected to the gastric band.

8. The gastric band securing device of claim 7, wherein the at least one hole is configured to allow the gastric tissue and the other gastric tissue to be sutured to each other.

9. The gastric band securing device of claim 8, wherein the at least one hole is configured such that an upper part of the portion of the stomach is exposed through the at least one hole and sutured with a lower part of the portion of the stomach disposed below the main body.

10. The gastric band of claim 1, wherein the main body has a circular cross-section.

11. A gastric band comprising:
a band body; and
the gastric band securing device of claim 1.

12. The gastric band of claim 11, further comprising a tube mounted on an inside of the band body,
wherein the tube is configured to receive and output a fluid used to control a diameter of the inlet of the stomach.

13. The gastric band of claim 11, wherein a gap between a lower end portion of the main body and a lower end portion of the band body is 0.2-4 cm.

14. The gastric band of claim 11, wherein hardness of the linking structure is lower than that of the main body.

15. The gastric band of claim 14, wherein the hardness of the linking structure ranges from 15 A to 20 A, and the hardness of the main body ranges from 35 A to 45 A.

16. The gastric band of claim 11, wherein the at least one hole is configured to allow the gastric tissue and the other gastric tissue to be sutured to each other.

17. The gastric band of claim 16, wherein the at least one hole is configured such that an upper part of the portion of the stomach is exposed through the at least one hole and sutured with a lower part of the portion of the stomach disposed below the main body.

18. The gastric band of claim 11, wherein the linking structure has an annular shape and configured to wrap the gastric band to be connected to the gastric band.

19. The gastric band of claim 18, wherein the at least one hole is configured to allow the gastric tissue and the other gastric tissue to be sutured to each other.

20. The gastric band of claim 19, wherein the at least one hole is configured such that an upper part of the portion of the stomach is exposed through the at least one hole and sutured with a lower part of the portion of the stomach disposed below the main body.

* * * * *